United States Patent
Hughes et al.

(10) Patent No.: US 12,083,301 B2
(45) Date of Patent: Sep. 10, 2024

(54) FLUID DISPENSING APPARATUS FOR IRRIGATING A BODY CAVITY

(71) Applicant: DUCO LLC, Hempstead, NY (US)

(72) Inventors: Cameron Hughes, Hempstead, NY (US); James Pezzino, Brooklyn, NY (US); Justin Angel, New York, NY (US)

(73) Assignee: DUCO LLC, Hempstead, NY (US)

( * ) Notice: Subject to any disclaimer, the term of this patent is extended or adjusted under 35 U.S.C. 154(b) by 286 days.

(21) Appl. No.: 17/876,166

(22) Filed: Jul. 28, 2022

(65) Prior Publication Data

US 2023/0032289 A1 Feb. 2, 2023

Related U.S. Application Data

(60) Provisional application No. 63/226,275, filed on Jul. 28, 2021.

(51) Int. Cl.
*A61M 3/02* (2006.01)

(52) U.S. Cl.
CPC ........ *A61M 3/0245* (2013.01); *A61M 3/0262* (2013.01); *A61M 3/0283* (2013.01); *A61M 2210/0618* (2013.01); *A61M 2210/1067* (2013.01); *A61M 2210/1475* (2013.01)

(58) Field of Classification Search
CPC .............. A61M 3/0245; A61M 3/0262; A61M 3/0283; A61M 2210/0618; A61M 2210/1067; A61M 2210/1475
See application file for complete search history.

(56) References Cited

U.S. PATENT DOCUMENTS

| | | | | |
|---|---|---|---|---|
| 2,664,893 A | * | 1/1954 | Kempel | A61M 3/0262 206/229 |
| 3,530,858 A | * | 9/1970 | Edwards | A61M 3/0262 604/212 |
| 3,626,939 A | * | 12/1971 | Maltenfort | A61M 3/0262 222/215 |
| 3,651,808 A | * | 3/1972 | White | A61M 3/0287 604/213 |
| 3,688,766 A | * | 9/1972 | Kempel | A61M 3/0262 604/212 |
| 3,754,553 A | * | 8/1973 | Hewitt | A61M 3/0262 604/212 |
| 3,948,260 A | * | 4/1976 | Whipperman | A61M 3/0262 604/212 |
| 4,140,120 A | * | 2/1979 | Yamauchi | A61M 3/0262 4/443 |
| 4,223,810 A | * | 9/1980 | Sneider | A61M 3/0262 383/96 |
| 4,487,336 A | * | 12/1984 | Sneider | A61M 3/0262 383/96 |

(Continued)

*Primary Examiner* — Frederick C Nicolas
(74) *Attorney, Agent, or Firm* — Robert P. Michal, Esq.; Carter, DeLuca & Farrell LLP

(57) ABSTRACT

A fluid dispensing apparatus for irrigating a body cavity includes a fluid container assembly, a cap member, and a tip member. The fluid container assembly defines a longitudinal axis and includes a fluid container and an inlet assembly fixedly secured to the fluid container. The cap member is selectively rotatably attached to the inlet assembly. The tip member is selectively attachable to the cap member in response to rotation of the tip member about the longitudinal axis of the fluid container assembly.

20 Claims, 18 Drawing Sheets

(56) References Cited

U.S. PATENT DOCUMENTS

| | | | | |
|---|---|---|---|---|
| 5,655,686 A | * | 8/1997 | Jermyn | ................ B05B 11/047 |
| | | | | 222/481.5 |
| 7,438,704 B1 | * | 10/2008 | Kawashima | ............ B29C 57/00 |
| | | | | 215/381 |
| 8,409,152 B2 | * | 4/2013 | Hair | .................... A61M 3/0279 |
| | | | | 128/200.14 |
| 8,888,752 B2 | * | 11/2014 | Cacka | .................... A61H 35/04 |
| | | | | 604/514 |
| 8,991,660 B2 | * | 3/2015 | Hair | ........................ B65D 1/32 |
| | | | | 222/211 |
| 2003/0140408 A1 | * | 7/2003 | Chung | ................ A61M 3/0258 |
| | | | | 4/443 |

* cited by examiner

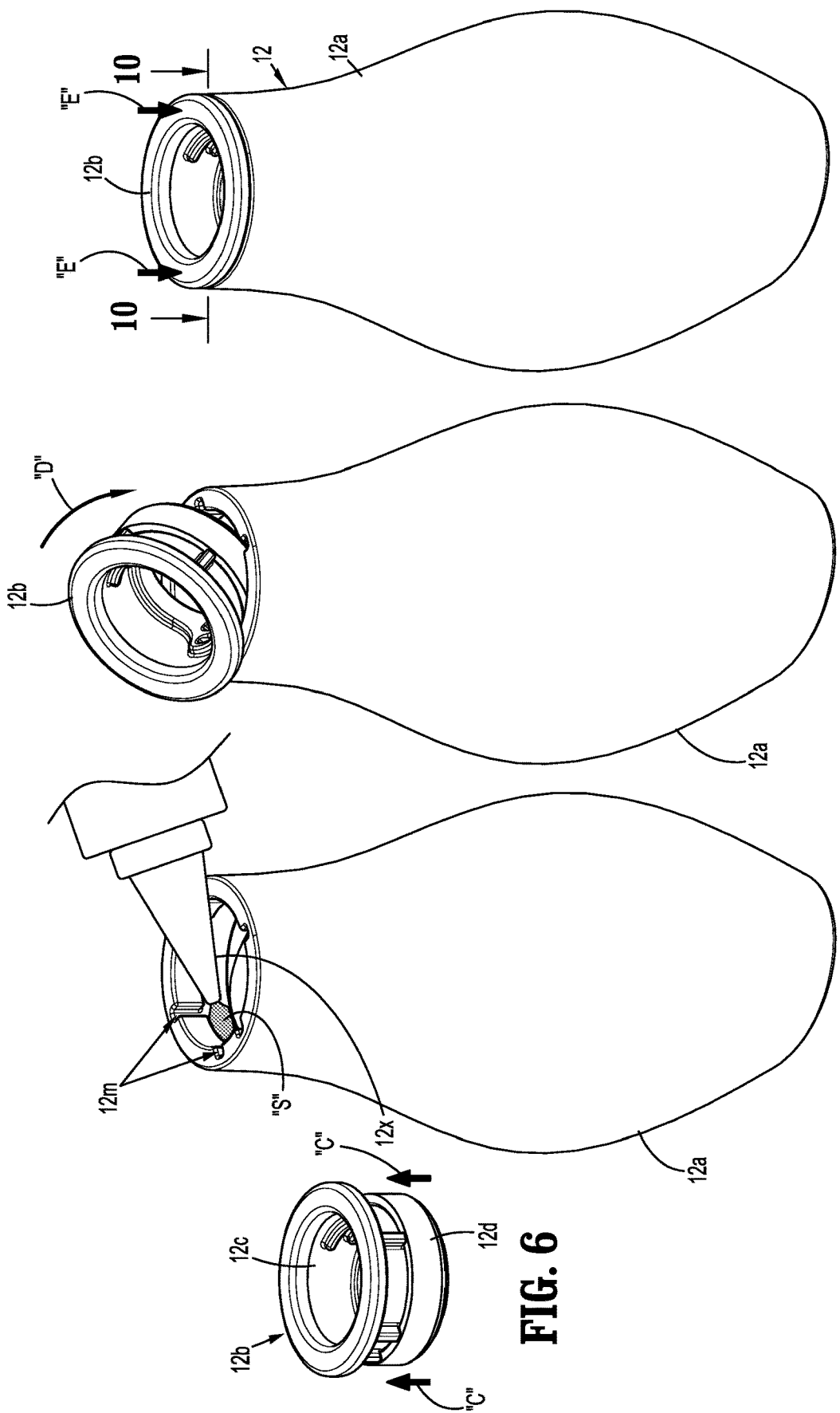

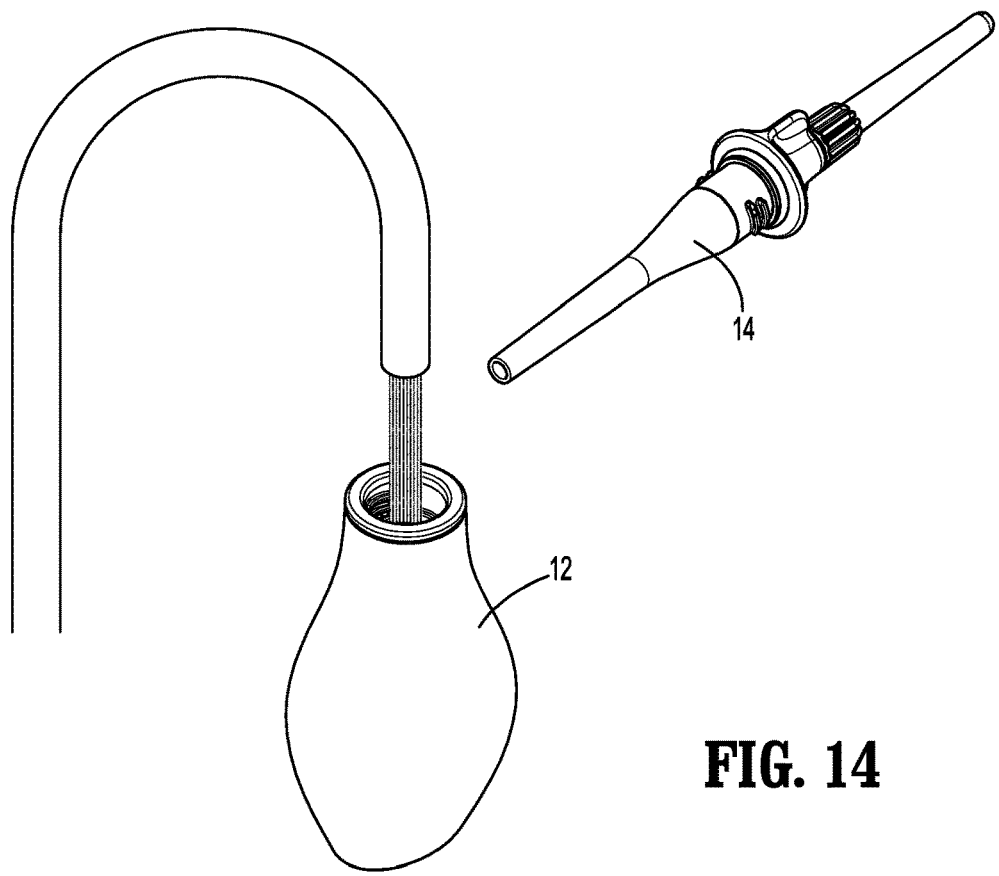
FIG. 14
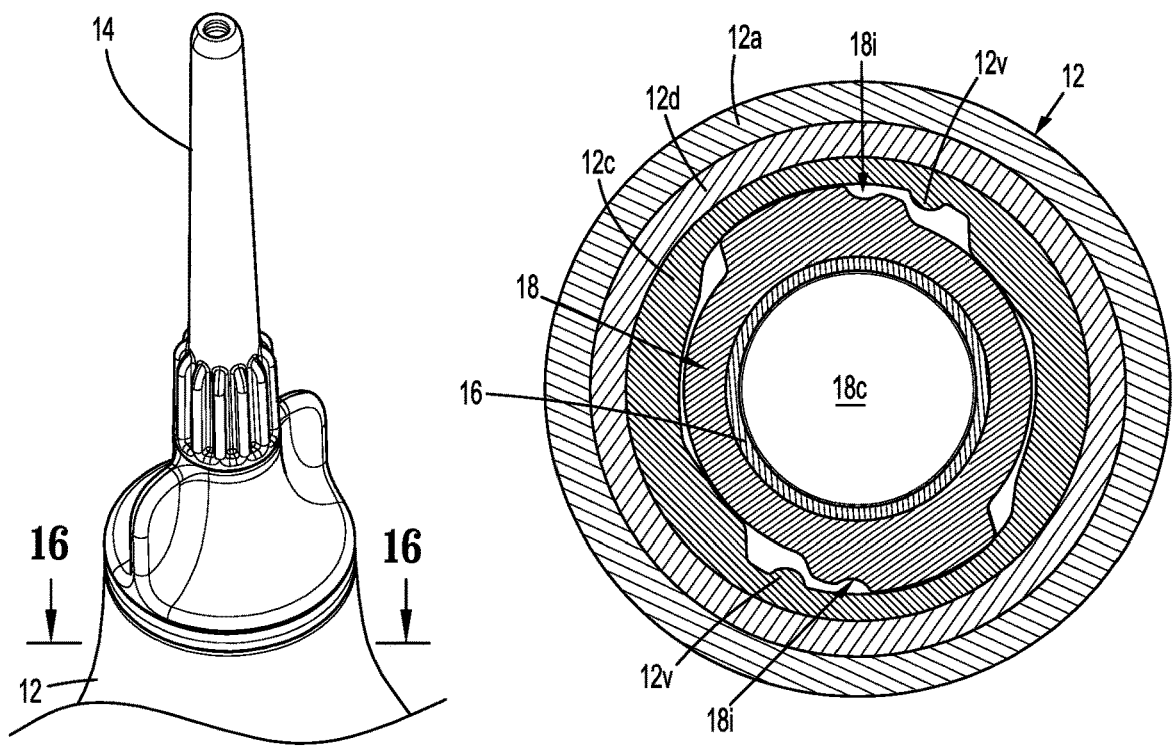
FIG. 15
FIG. 16

FLUID DISPENSING APPARATUS FOR IRRIGATING A BODY CAVITY

CROSS REFERENCE TO RELATED APPLICATIONS

This application claims the benefit of U.S. Provisional Patent Application No. 63/226,275, filed Jul. 28, 2021, the entire contents of which are incorporated by reference herein.

TECHNICAL FIELD

This disclosure relates to fluid dispensing apparatus, and more particularly, to fluid dispensing apparatus for dispensing fluid in body cavities such as rectal, vaginal, or nasal cavities, for example, to clean, rinse, and/or hydrate such cavities.

BACKGROUND

Fluid dispensing apparatus, such as douche devices, have long been used to clean body cavities. When enemas are effectuated, for instance, many fluid dispensing devices include a bulb or bag of water that is coupled to a non-replaceable dispensing tip used to irrigate the rectal cavity. Such bulbs and/or bags have small openings that are difficult to open and fill, and once the procedure is completed, the fluid dispensing device, or substantial portions thereof may be discarded or reused.

SUMMARY

According to an aspect of this disclosure, a fluid dispensing apparatus for irrigating a body cavity includes a fluid container assembly, a cap member, and a tip member. The fluid container assembly defines a longitudinal axis and includes a fluid container and an inlet assembly fixedly secured to the fluid container. The inlet assembly and the fluid container have different materials than one another. The cap member is selectively rotatably attached to the inlet assembly. The tip member is selectively attachable to the cap member in response to rotation of the tip member about the longitudinal axis of the fluid container assembly.

In aspects, the fluid dispensing apparatus may further include a straw member that is selectively rotatably attached the cap member.

In aspects, the cap member may define a central passage that supports a one-way valve assembly that is disposed in fluid communication with the tip member and a fluid cavity of the fluid container.

In aspects, the cap member may include an actuator portion having a pair of opposed wings that extends from an external surface of the cap member for facilitating rotatable movement of the cap member relative to the fluid container. The actuator portion may include a locking device that extends radially inward from an inner surface of the cap member that defines the central passage. The locking device may be configured to secure a proximal end portion of the tip member within the cap member. The proximal end portion of the tip member may include a coupling portion. The coupling portion of the tip member may include elongated tabs that project radially outward from an outer side surface of the coupling portion. The elongated tabs may be configured to cooperate with the locking device within the actuator portion of the cap member to facilitate the selective securement of the coupling portion of the tip member within the cap member.

In aspects, the cap member may include a coupling portion that extends proximally from the actuator portion of the cap member. The coupling portion of the cap member may include elongated tabs that project radially outward from an outer side surface of the coupling portion of the cap member. The elongated tabs of the cap member may be configured to cooperate with a locking device of the inlet assembly to selectively secure the cap member to the fluid container assembly. The locking device of the inlet assembly may include detents that cooperate with detent recesses defined in the elongated tabs of the cap member to facilitate the selective securement of the coupling portion of the cap member within the inlet assembly.

In aspects, the fluid dispensing apparatus may include at least one O-ring that fluidly seals a connection between the cap member and the fluid container, the cap member and the tip member, and/or the cap member and the straw member.

In aspects, the fluid dispensing apparatus may further include a silicone seal disposed on an inner surface of the fluid container between the inlet assembly and the fluid container to facilitate securement of the inlet assembly to the fluid container.

In aspects, the inlet assembly may include a plurality of spaced-apart ribs and the fluid container may define a plurality of rib channels that receive the plurality of spaced-apart ribs of the inlet assembly to facilitate the securement of the inlet assembly to the fluid container.

In aspects, the inlet assembly may include an upper lip and a lower lip. The upper lip may be positioned to seat on an end face of the fluid container. The lower lip may be positioned to support a gasket on an outer surface of the inlet assembly.

In aspects, the fluid container may include an air valve in a bottom surface of the fluid container.

In aspects, the fluid container may include a flexible material that is actuatable upon a squeezing thereof, wherein actuation of the fluid container actuates the one-way valve assembly to enable fluid to pass from the fluid container through the tip member for dispensing the fluid from the tip member. The air valve may enable air to enter into the fluid cavity when the fluid container moves from a squeezed position to an unsqueezed position.

According to another aspect, this disclosure is directed to a fluid dispensing system including a fluid container assembly and a cap assembly. The fluid container assembly includes a fluid container and an inlet assembly secured to the fluid container by a plurality of rib members extending into the fluid container. The cap assembly is selectively attached to the inlet assembly. The cap assembly includes at least one tip member and a straw member that are selectively rotatably attachable to the cap assembly. The straw member extends into the fluid container when secured to the cap assembly.

In aspects, the at least one tip member may include a first tip member and a second tip member.

In aspects, at least one of the first or second tip members may be disposable.

In aspects, the at least one tip member may include an angled tip member.

According to still another aspect, this disclosure is directed to a fluid dispensing system includes a fluid container and a cap assembly. The fluid container assembly includes a fluid container and an inlet assembly fixedly secured to the fluid container by a silicone seal. The cap assembly is selectively attached to the inlet assembly. The cap assembly includes at least one tip member having pairs of elongated tab members extending radially outward from an annular sidewall of the at least tip member. The pairs of elongated tabs members are selectively attachable to the cap assembly by a locking device within the cap assembly that interlocks with the pairs of elongated tab members of the at least one tip member.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, explain the principles of this disclosure, wherein:

FIG. 6 is an enlarged, perspective view of an inlet assembly of the fluid container assembly of FIG. 5;

FIGS. 7-9 are progressive views illustrating the inlet assembly of FIG. 6 being secured to a fluid container of the fluid container assembly of FIG. 5;

FIG. 14 is a perspective view illustrating the fluid container assembly of FIG. 5 being filled with fluid with the cap assembly of the fluid dispenser apparatus of FIGS. 1 and 2 removed from the fluid container assembly of the fluid dispenser apparatus;

FIGS. 15-18 are progressive views illustrating the cap assembly of FIG. 3 being secured to the fluid container assembly of FIG. 3;

DETAILED DESCRIPTION

Figure 1:
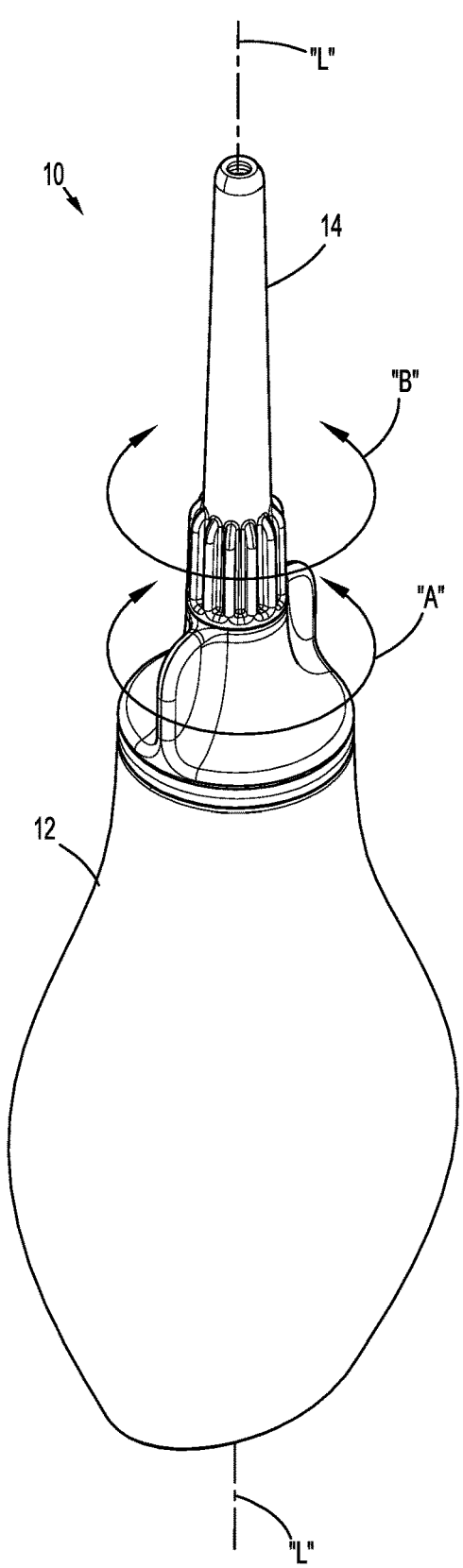
FIG. 1 is a top perspective view of a fluid dispensing apparatus in accordance with the principles of this disclosure.
Figure 2:
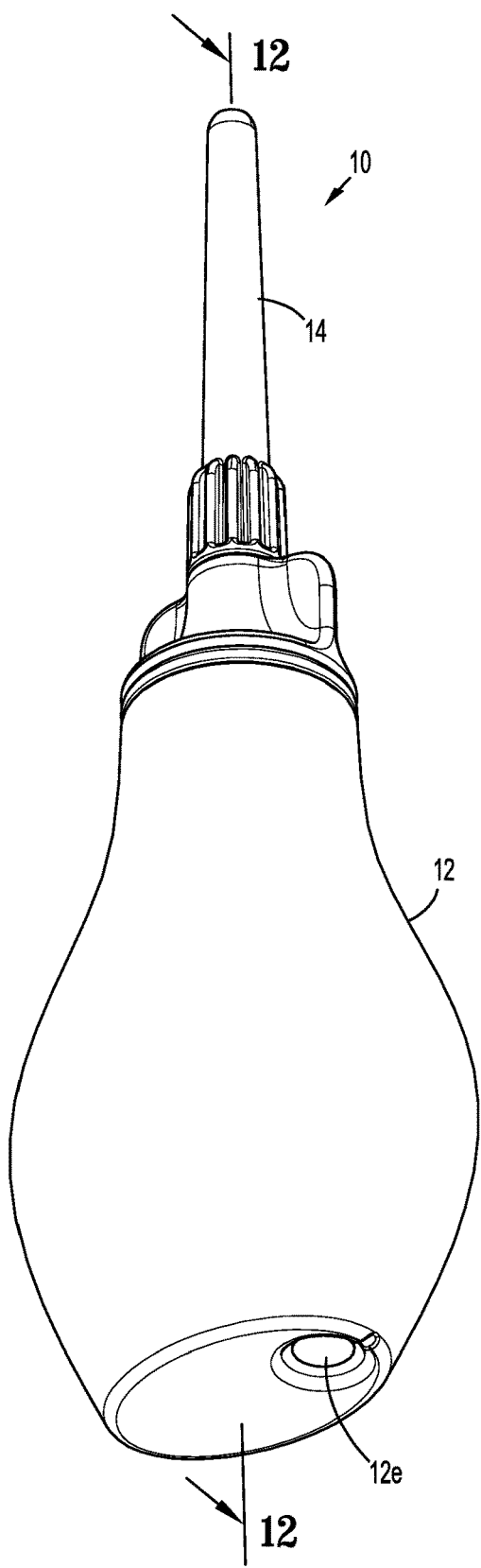
FIG. 2 is a bottom perspective view of the fluid dispensing apparatus of FIG. 1.
Figure 3:
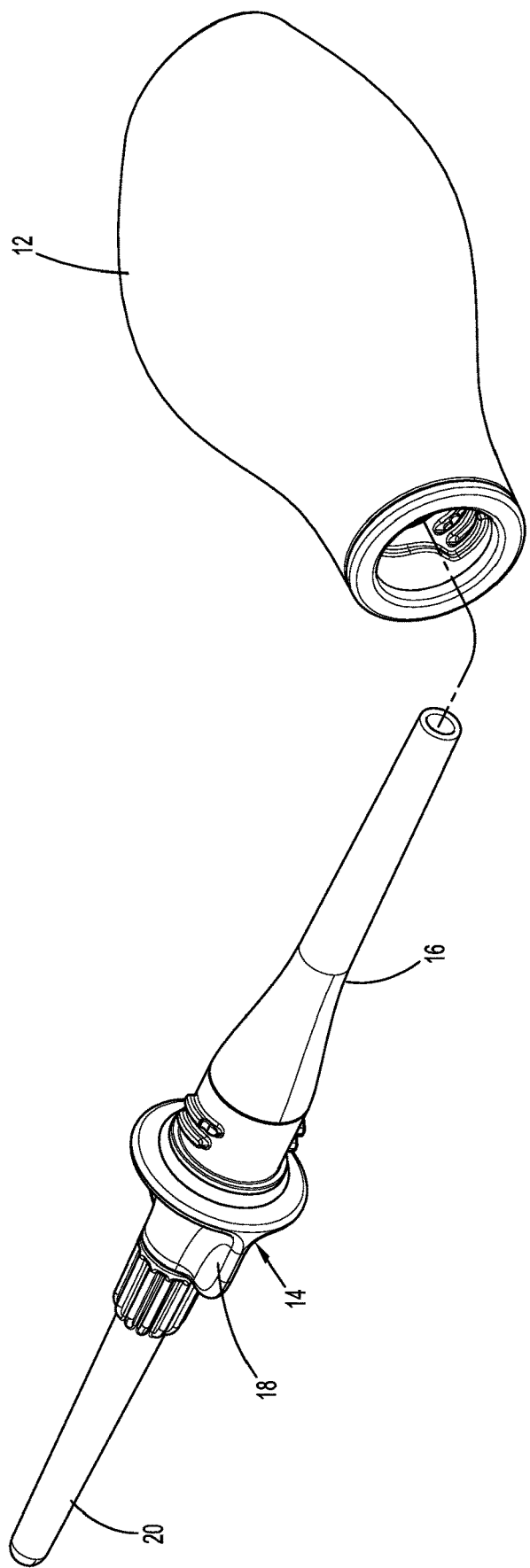
FIG. 3 is perspective view of the fluid dispensing apparatus of FIGS. 1 and 2 with a cap assembly of the fluid dispensing apparatus shown separated from a fluid container assembly of the fluid dispensing apparatus.

Aspects of this disclosure are described in detail with reference to the drawings, in which like reference numerals designate identical or corresponding elements in each of the several views. As used herein, the term "distal" refers to that portion of structure closer to a user, while the term "proximal" refers to that portion of structure, farther from the user.

In the following description, well-known functions or constructions are not described in detail to avoid obscuring the present disclosure in unnecessary detail.

With reference to FIGS. 1 to 20, a fluid dispensing apparatus 10 defines a longitudinal axis "L" and includes a fluid container assembly 12 and a cap assembly 14 that is selectively rotatably attachable to the fluid container assembly 12.

As best seen in FIGS. 3, 4, 12, and 13, the cap assembly 14 of the fluid dispensing apparatus 10 includes a straw member 16, a cap member 18, and a tip member 20. The tip member 20 and the straw member 16 are selectively attachable to the cap member 18. In particular, the straw member 16 may be selectively removed from the cap member 18 to enable the fluid dispensing apparatus 10 to dispense fluid "F" from the fluid dispensing apparatus 10 in either upright and/or downright positions, depending on whether the straw member 16 is attached to the cap member 14 when the cap member 14 is secured to the fluid container assembly 12. A one-way valve assembly 22 is supported between the cap member 18 and the straw member 16 to prevent, for example, external debris and/or bodily fluids from entering into the fluid container 12a (e.g., upon insertion of tip member 20 into a body cavity). The cap assembly 14 further includes O-rings 24a, 24b, and 24c that function to seal the cap assembly 14 when the straw member 16, the cap member 18, and the tip member 20 are coupled together.

The straw member 16 of the cap assembly 14 includes an elongated member 16a on a proximal end portion and a connector portion 16b on a distal end portion. The elongated member 16a of the straw member 16 has a straight segment 16c that extends from a proximal end of the straw member 16 to a conical portion 16d on a distal end of the elongated member 16a. The conical portion 16d couples the elongated member 16a to the connector portion 16b. The straw member 16 defines a central longitudinal passage 16e that extends through the straw member 16 from the proximal end of the straw member 16 to the distal end of straw member 16. The connector portion 16b includes a ledge 16f that is spaced-apart from a distal end face 16g of the conical portion 16d to define a first O-ring channel 16h for supporting the O-ring 24a. The connector portion 16 further includes a first elongated tab 16i that extends radially outward from an annular sidewall 16k of the connector portion 16b on a first side of the connector portion 16b and a second elongated tab 16j that extends radially outward from the annular sidewall 16k of connector portion 16b on a second side of the connector portion 16b. The first and second elongated tabs 16i, 16j each having first and second end portions that extend to respective first and second ends. The first end portion of the first elongated tab 16i is angularly displaced from the second end portion of the first elongated tab 16*i*, and the first end portion of the second elongated tab 16*j* is angularly displaced from the second end portion of the second elongated tab 16*j*. The first elongated tab 16*i* defines a first detent recess 16*m* in the first end portion of the first elongated tab 16*i*. The second elongated tab 16*j* defines a second detent recess 16*n* in the second end portion of the second elongated tab 16*j* such that the first and second detent recesses 16*m*, 16*n* of the respective first and second elongated tabs 16*i*, 16*j* are disposed in mirrored relationship about a central longitudinal plane (not shown) defined through the straw member 16. The first and second detent recesses 16*m*, 16*n* are both angularly displaced from the respective first and second ends of the respective first and second elongated tabs 16*i*, 16*j*. As can be appreciated, any of the described elongated tabs may be in the form of a quick turn thread.

With reference to FIGS. 4 and 4A to 4C, the cap member 18 of the cap assembly 14 includes a coupling portion 18*a* that enables selective removal and/or attachment of the straw member 16 to the cap member 18, and an actuator portion 18*b* that enables selective removal and/or attachment of the tip member 20 and which provides leverage for rotating the cap member 18 onto and/or off of the fluid container assembly 12. The cap member 18 defines a central passage 18*c* that extends through the coupling portion 18*a* and the actuator portion 18*b* for enabling the passage of fluid "F" therethrough. The central passage 18*c* includes a valve segment 18*d* configured to support the valve assembly 22 and a tip segment 18*e* configured to support a proximal end portion of the tip member 20 of the cap assembly 14.

The coupling portion 18*a* of the cap member 18 includes a first pair of elongated tabs 18*f*, 18*g* on an outer surface of an annular sidewall 18*h* of the coupling portion 18*a*. The elongated tab 18*f* is vertically spaced part from the elongated tab 18*g* by a gap 18*i*. The elongated tabs 18*f*, 18*g* extend radially outward from the annular sidewall 18*h* on a first side of the coupling portion 18*a*. The elongated tabs 18*f*, 18*g* are substantially similar, but the elongated tab 18*g* is longer than the elongated tab 18*f* and further includes a first detent recess 18*j* defined in a first end portion of the elongated tab 18*g*. The coupling portion 18*a* further includes a second pair of elongated tabs 18*m*, 18*n* disposed on an opposite side of coupling portion 18*a* than the first pair of elongated tabs 18*f*, 18*g*. The second pair of elongated tabs 18*m*, 18*n* are disposed in mirrored relationship to the first pair of elongated tabs 18*f*, 18*g* about a central longitudinal plane (not shown) defined through the cap member 18, and are otherwise identical to the first pair of elongated tabs 18*f*, 18*g* (see FIG. 13). The first and second pair of elongated tabs function to selectively secure the cap member 18 to the fluid container assembly 12, namely to an inlet assembly 12*b* of the fluid container assembly 12. The coupling portion 18*a* further includes an inner surface 19 defining locking channels 19*a*, 19*b* in the inner surface 19 that each include detents 19*c* along a portion of the respective locking channels 19*a*, 19*b*. The locking channels 19*a*, 19*b* function to enable the cap member 18 to selectively attach to the straw member 16.

Figure 20:
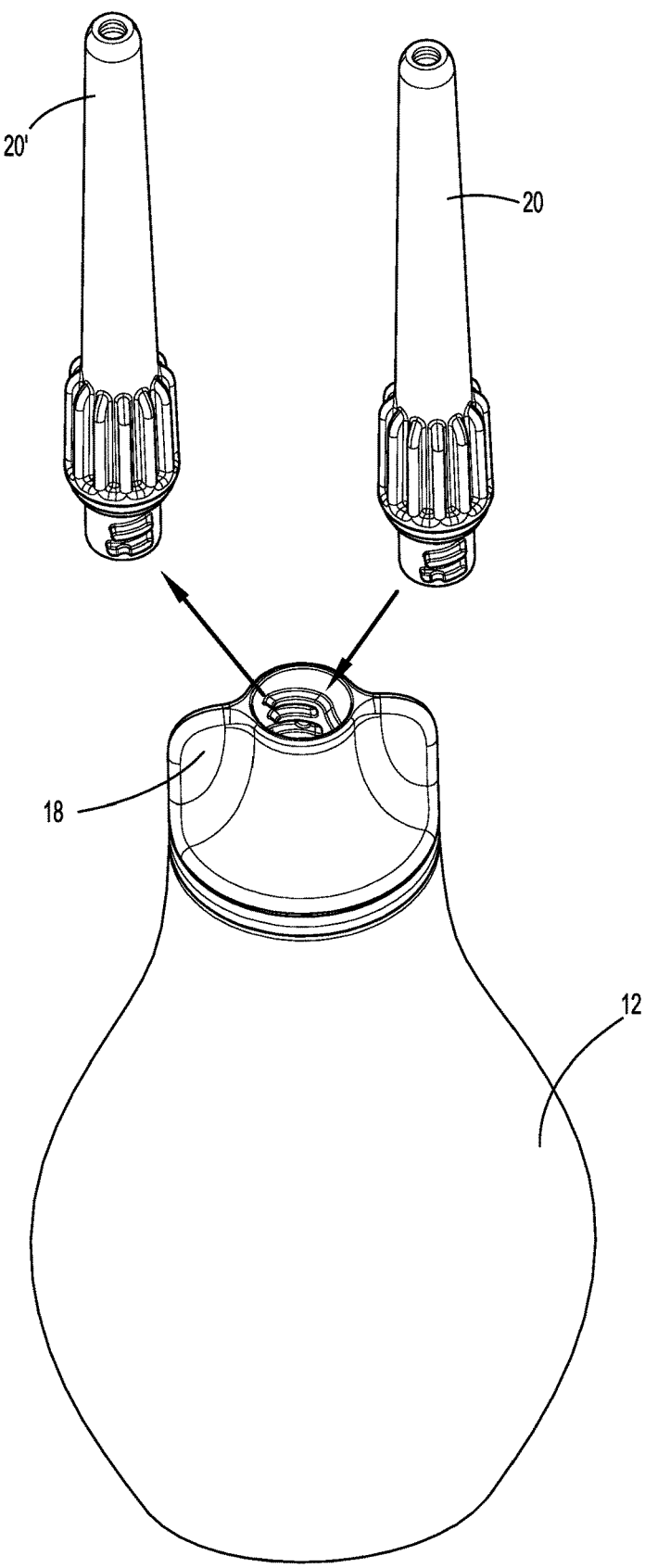
FIG. 20 is a perspective view of a fluid dispensing system in accordance with the principles of this disclosure.

The actuator portion 18*b* of the cap member 18 includes diametrically opposed actuator wings 18*p* that extend radially outward from the cap member 18 to facilitate rotation of the cap member 18 relative to the fluid container assembly 12, as indicated by arrows "A" (FIG. 17), when wings 18*p* of the cap member 18*a* are rotated about longitudinal axis "L" of fluid dispensing apparatus 10. In particular, the wings 18*p* provide leverage to the user when opening and/or closing the fluid dispensing apparatus 10 (e.g., removing and/or attaching the cap assembly 14 to the fluid container assembly 12). The actuator portion 18*b* further includes a locking device 18*q* that extends radially inward from an inner surface 18*r* of the cap member 18 and functions to enable tip member 20 to selectively lockingly attach to the cap member 18. The inner surface 18*r* of the cap member 18 defines the tip segment 18*e* of the central passage 18*c* of the cap member 18. As best seen in FIG. 20, the locking device 18*q* includes a pair of hands 18*w*, 18*x* supported on the inner surface 18*r* of cap member 18 with each of the pair of hands 18*w*, 18*x* being disposed on one side of the inner surface 18*r* of the cap member 18 so that the pair of hands 18*w*, 18*x* is disposed in mirrored relationship with one another on opposite sides of the inner surface 18*r* of the actuator portion 18*b* of the cap member 18 (e.g., diametrically opposed). Each of the pair of hands 18*w*, 18*x* includes fingers 18*s* that are separated by tab channels 18*t* defined between the fingers 18*s*. Detents 18*v*, 18*y* are disposed in respective lower-most tab channels 18*z*, 18*zz* of each of the pair of hands 18*w*, 18*x*.

Figure 4:
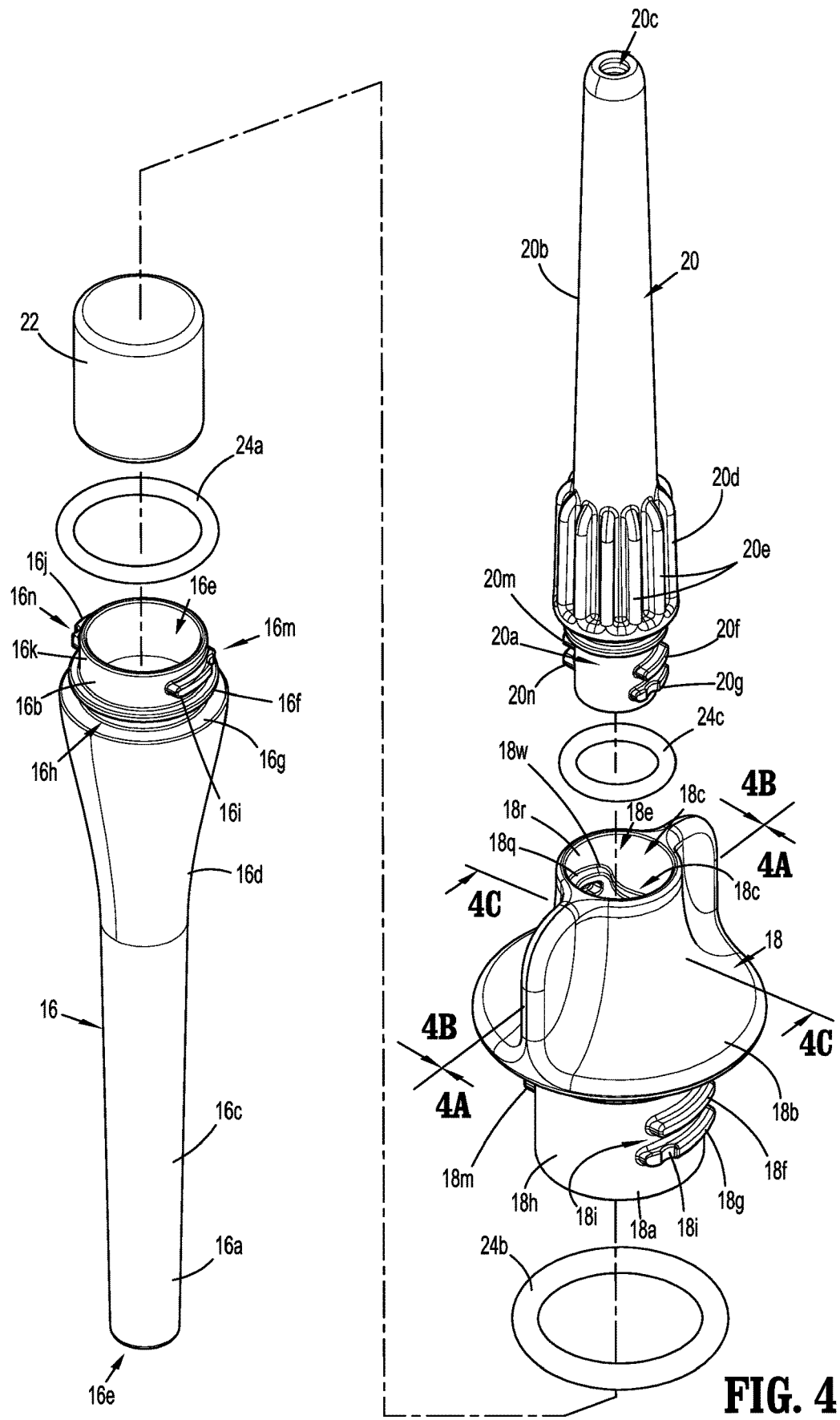
FIG. 4 is an enlarged, perspective view, with parts separated, of the cap assembly of FIG. 3.
Figure 4A:
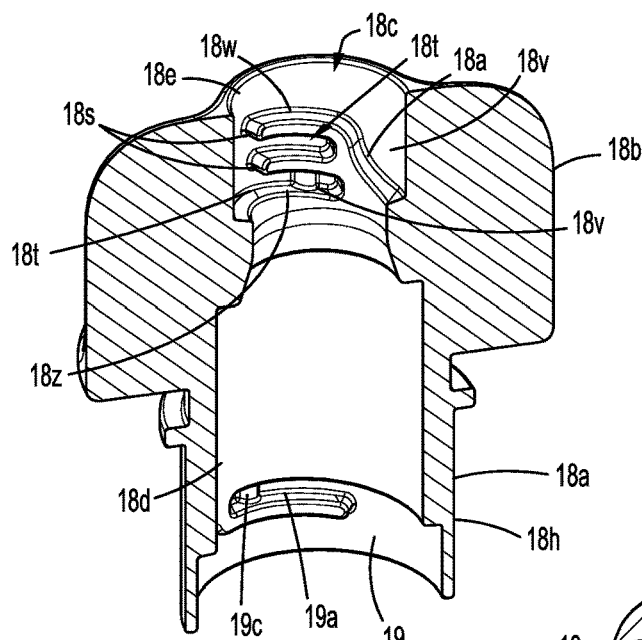
FIGS. 4A-4C are cross-sectional views as taken along the respective lines 4A-4A, 4B-4B, and 4C-4C shown in FIG. 4.
Figure 4B:
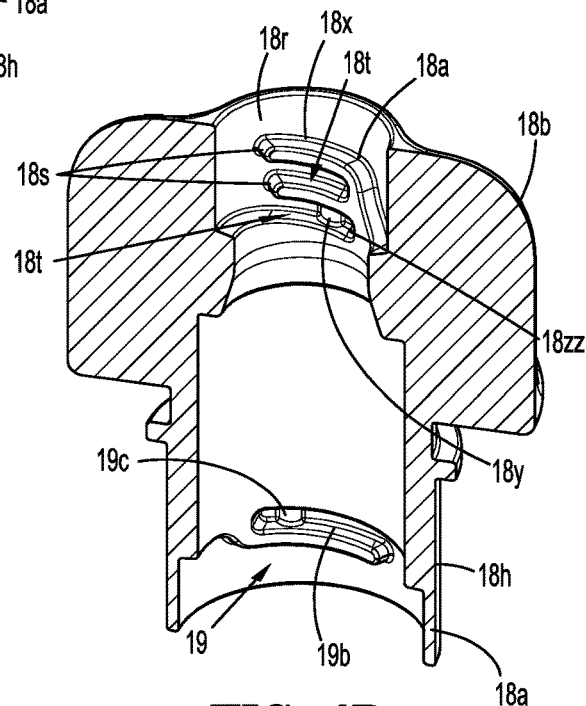
Figure 4C:
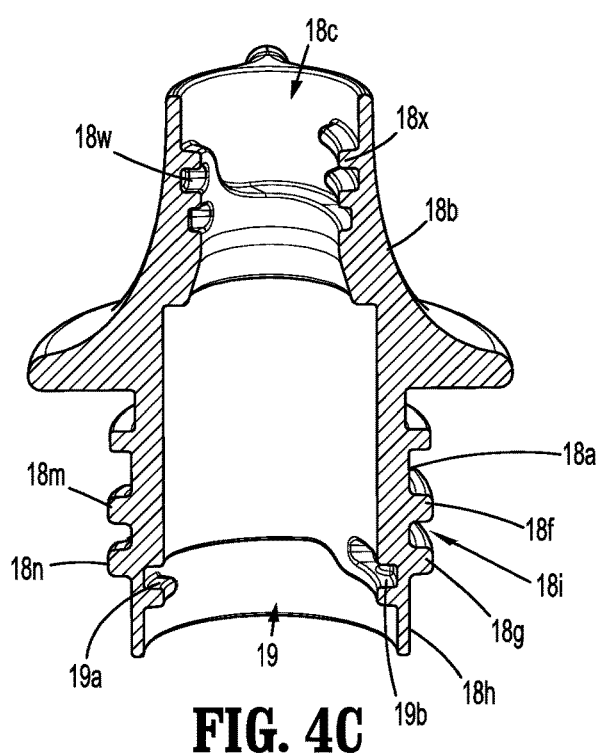
Figure 5:
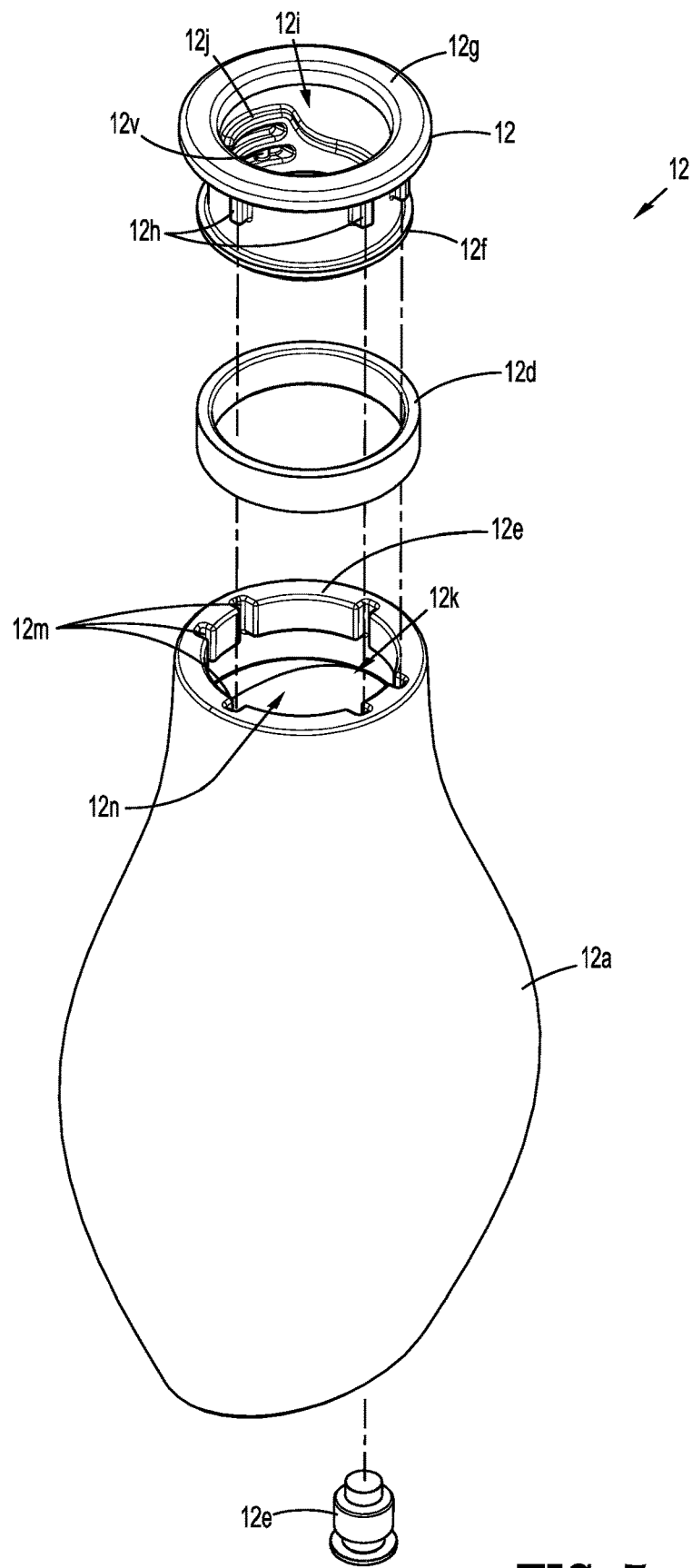
FIG. 5 is an enlarged, perspective view, with parts separated, of the fluid container assembly of FIG. 3.
Figure 12:
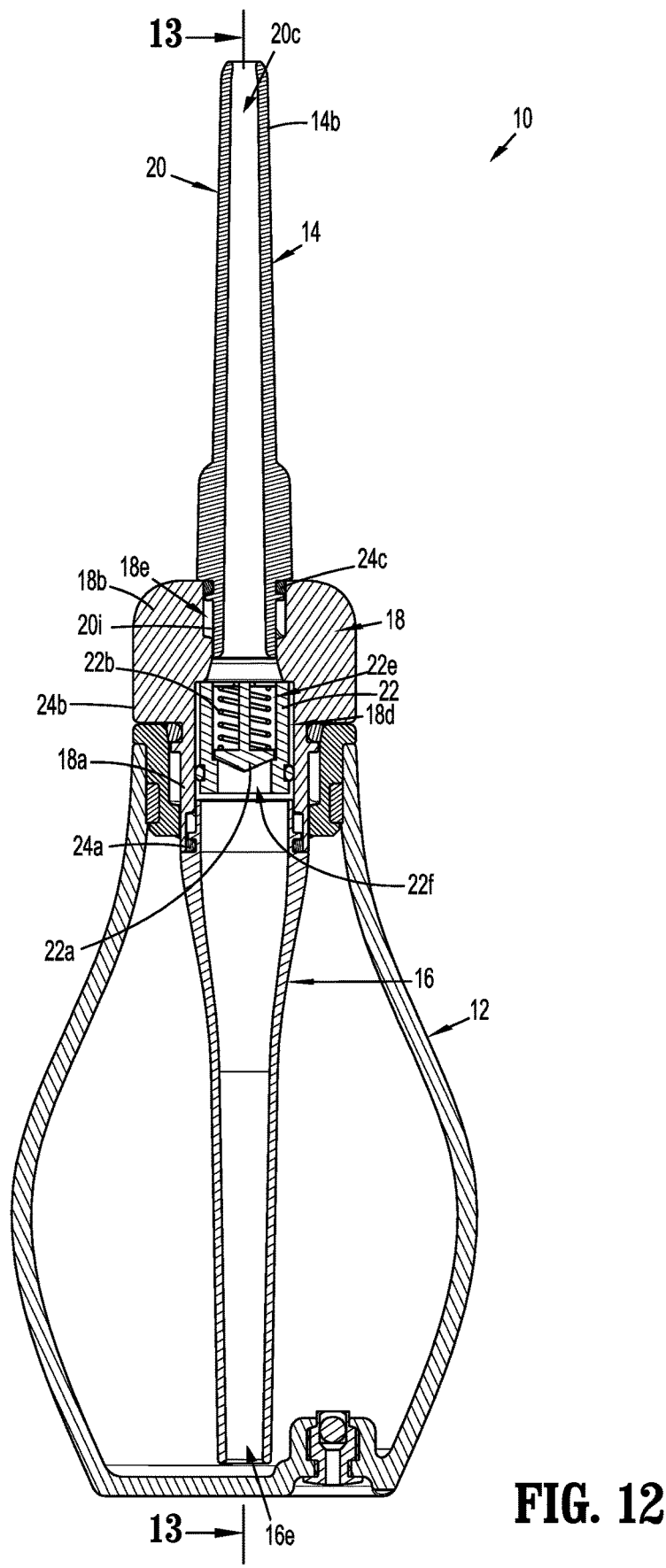
FIG. 12 is a cross-sectional view as taken along section line 12-12 shown in FIG. 2.
Figure 13:
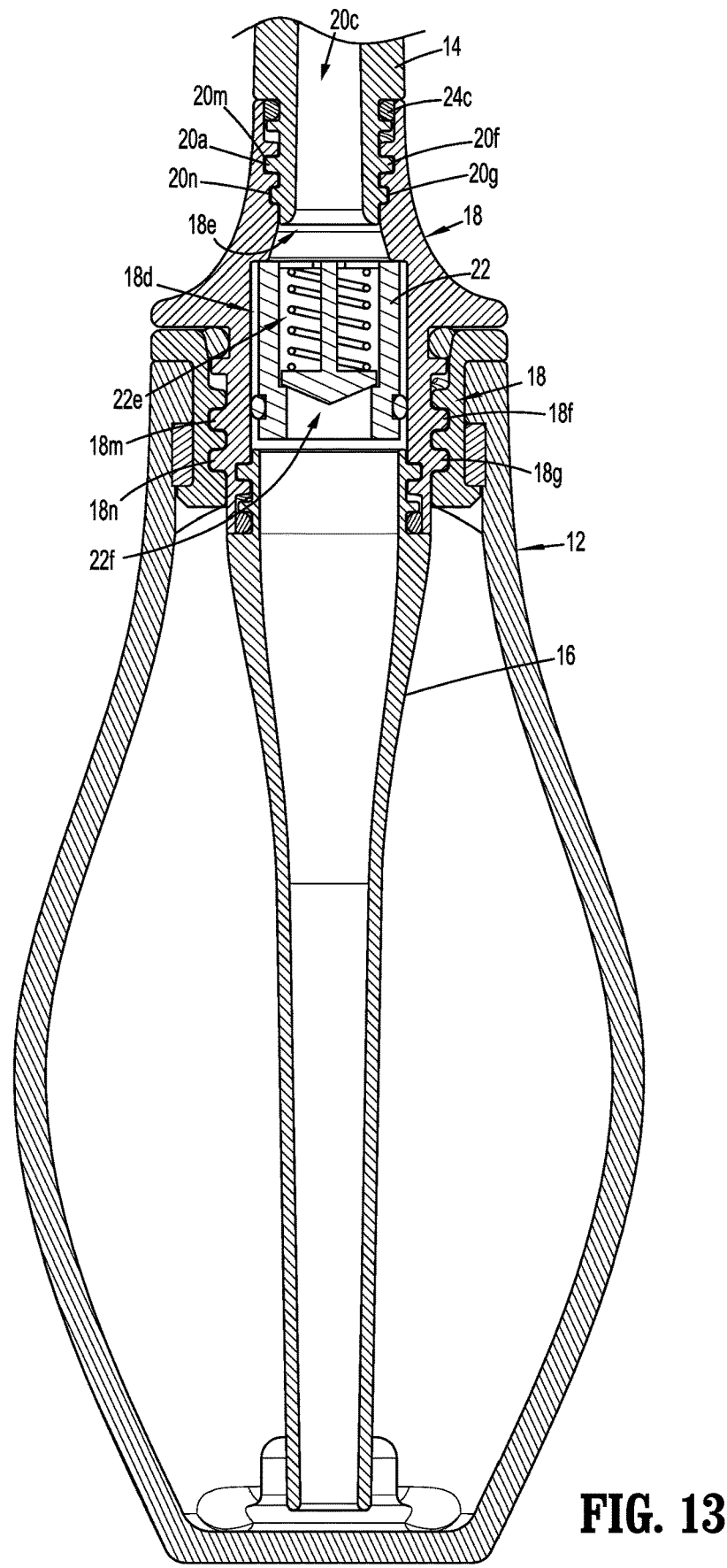
FIG. 13 is an enlarged cross-sectional view as taken along section line 13-13 shown in FIG. 12.

As seen in FIGS. 4, 12, and 13, the tip member 20 of the cap assembly 14 includes a coupling portion 20*a* on a proximal end portion and an elongated shaft 20*b* on a distal end portion. The tip member 20 further defines a central passage 20*c* that extends through the coupling portion 20*a* and the elongated shaft 20*b*. A gripping portion 20*d* including a plurality of spaced-apart ribs 20*e* circumscribes a proximal end portion of the elongated shaft 20*b* to enable the tip member 20 to be rotated about longitudinal axis "L", as indicated by arrows "B" (see FIG. 1), to selectively secure the tip member 20 to the cap member 18. The coupling portion 20*a* further includes first and second pairs of elongated tabs 20*f*, 20*g* and 20*m*, 20*n* that are substantially similar to the first and second pairs of elongated tabs 18*f*, 18*g* and 18*m*, 18*n* of the cap member 18, but are smaller in dimension (e.g., length, width, height, etc.). The first and second pairs of the elongated tabs 20*f*, 20*g* and 20*m*, 20*n* of the tip member 20 are configured to cooperate and selectively mate with locking device 18*q*, namely the pair of hands 18*w*, 18*x*, of the cap member 18 when the tip member 20 is rotated into and/or out of the tip segment 18*e* of the central passage 18*c* of the cap member 18, as indicated by arrows "B" (FIG. 1).

With reference to FIGS. 12 and 13, the one-way valve assembly 22 of the cap assembly 14 may be in the form of a check valve and includes a movable disc 22*a* and a spring 22*b*. The one-way valve assembly 22 defines a central passage 22*c* therethrough that includes a wide segment 22*e* along a distal portion of the one-way valve assembly 22 and a narrow segment 22*f* along a proximal portion of the one-way valve assembly 22. The spring 22*b* is configured to urge the movable disc 22*a* into a sealed relationship with a distal end of the narrow segment 22*f* to prevent fluid flow from the fluid container assembly 12 into the tip member 20.

Figure 17:
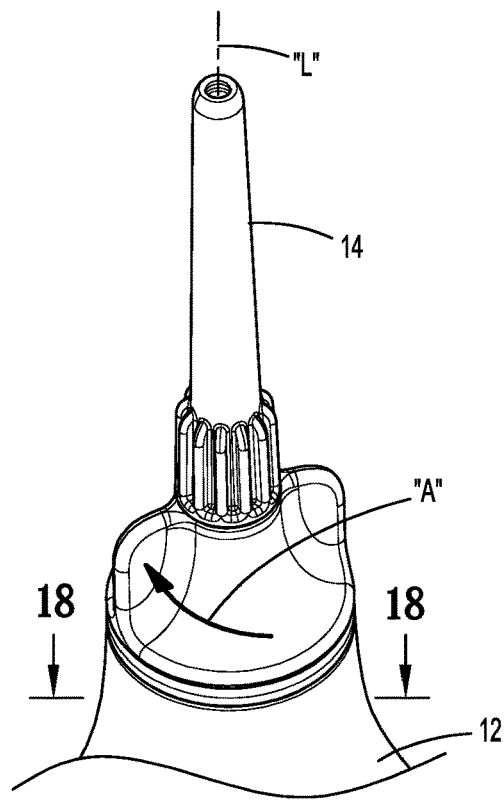
Figure 18:
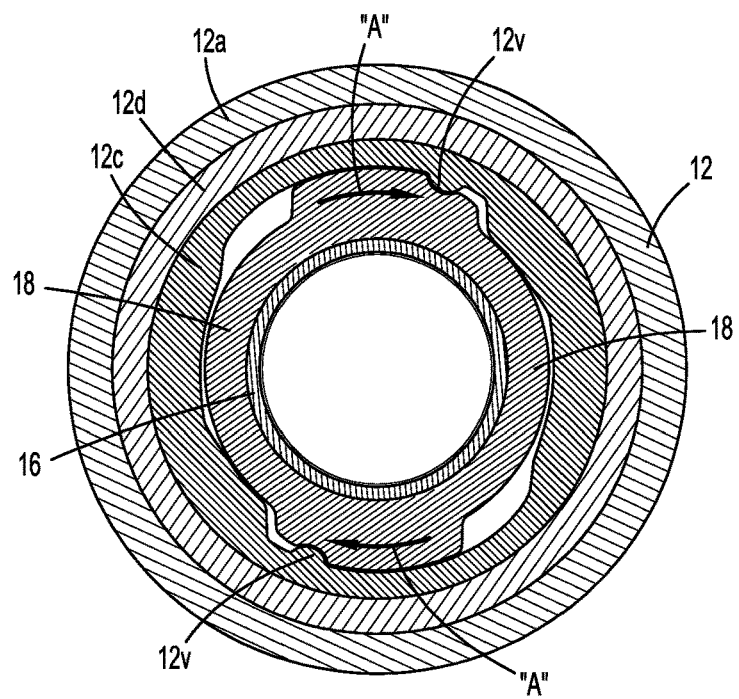
Figure 19:
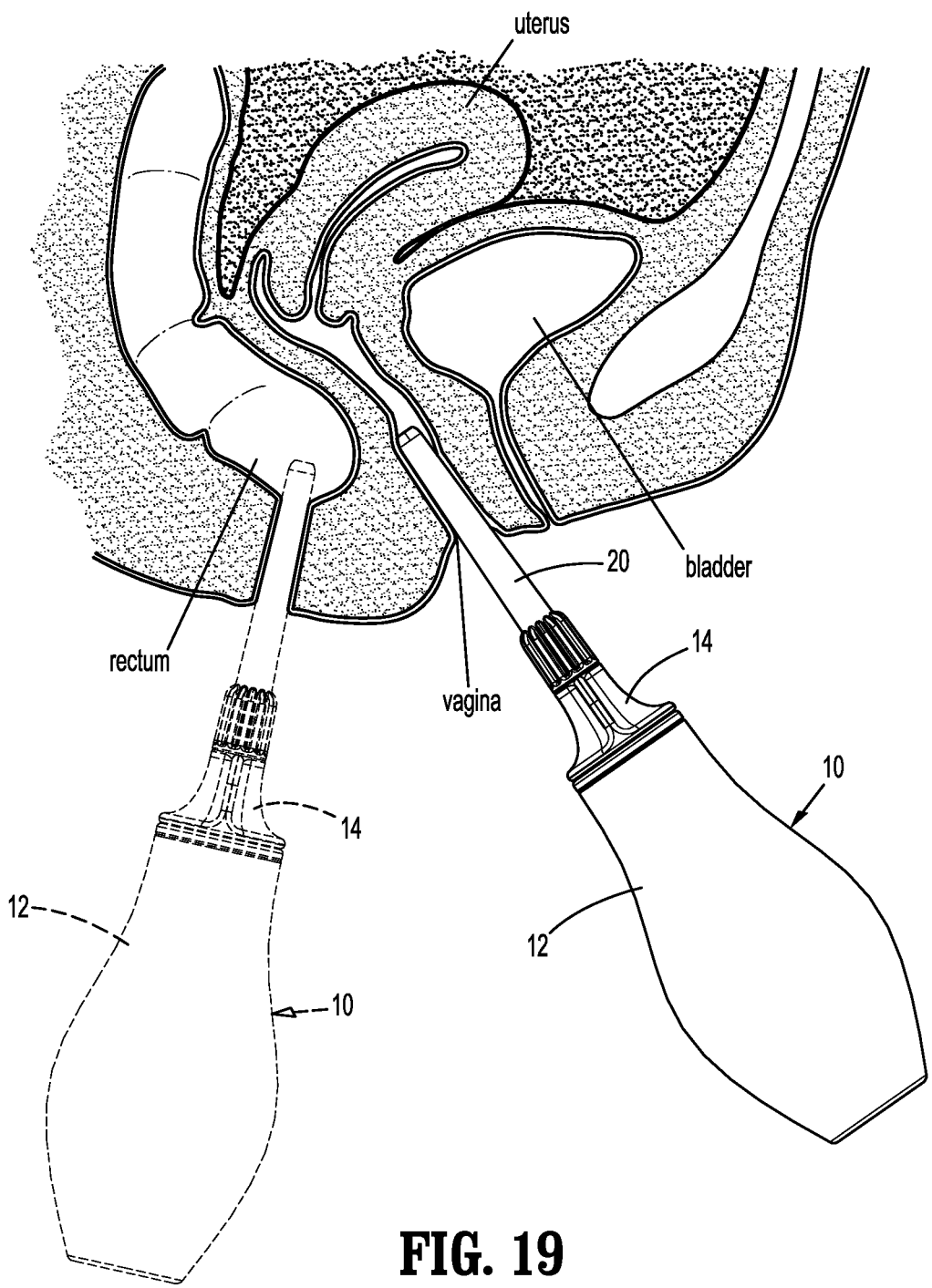
FIG. 19 is a view illustrating a tip assembly of the fluid dispensing apparatus of FIGS. 1 and 2 being inserted within body cavities for irrigating such cavities.
Figure 19A:
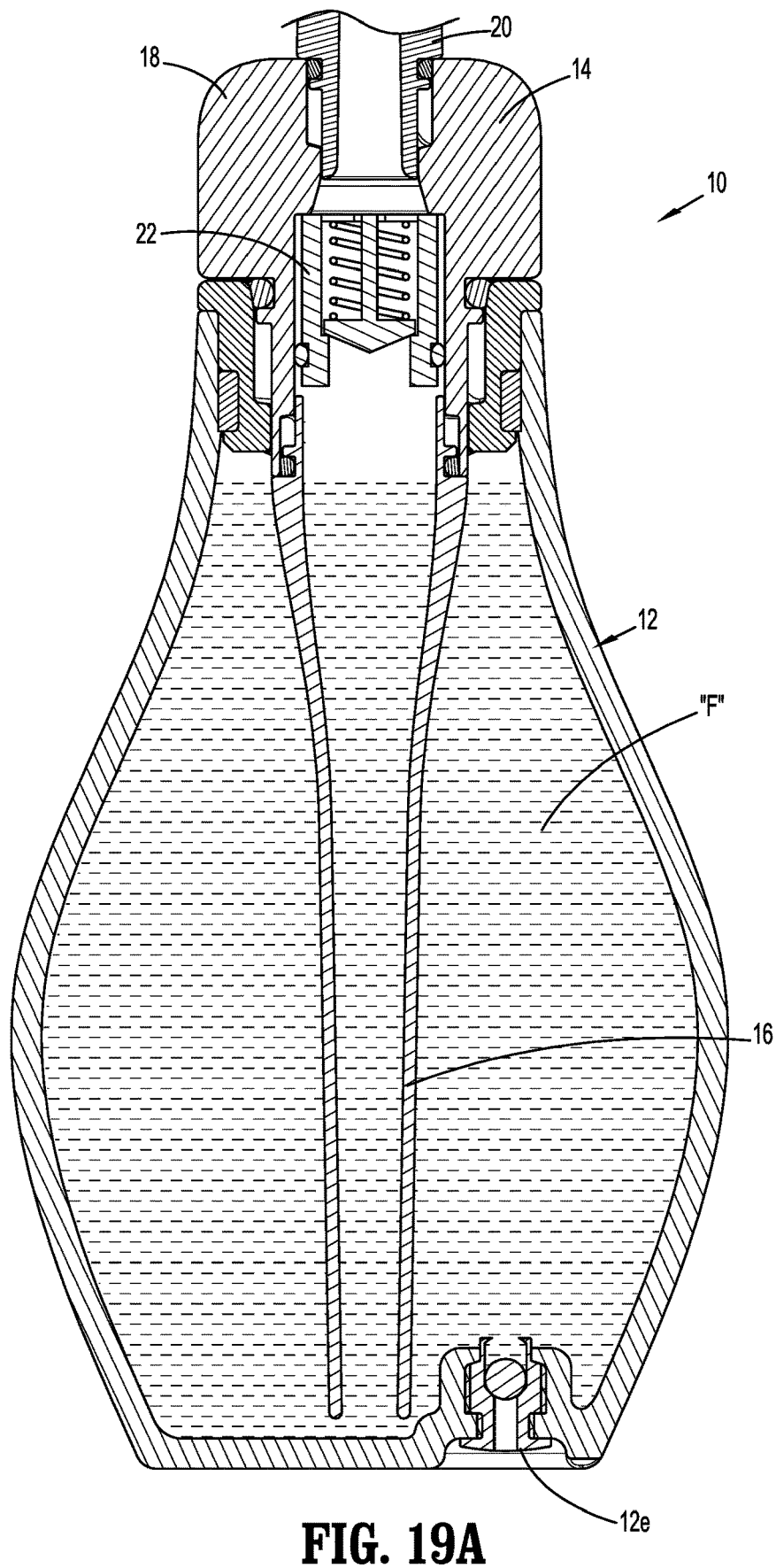
FIGS. 19A-19C are progressive views illustrating fluid being dispensed from the fluid dispensing apparatus of FIGS. 1 and 2.
Figure 19B:
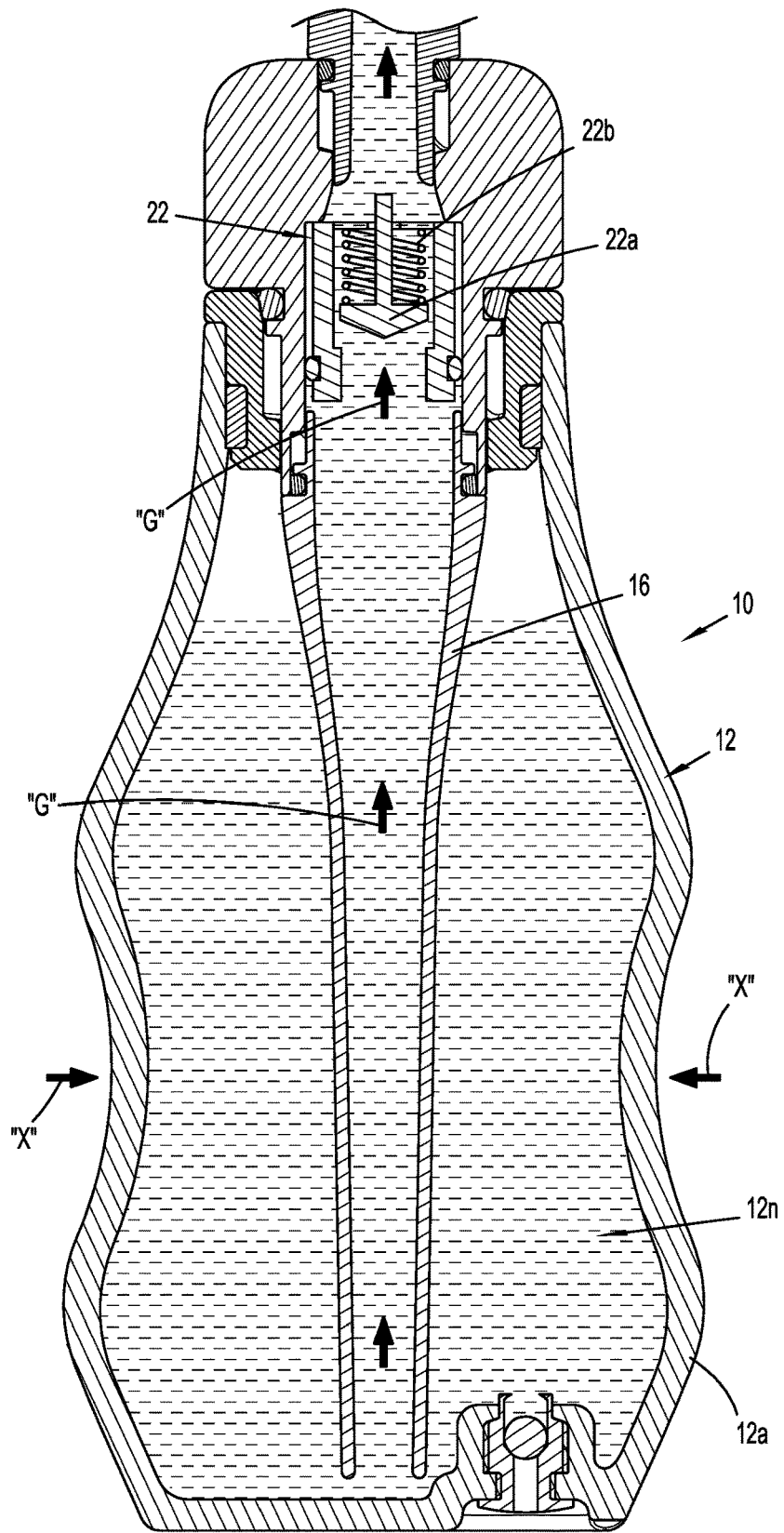
Figure 19C:
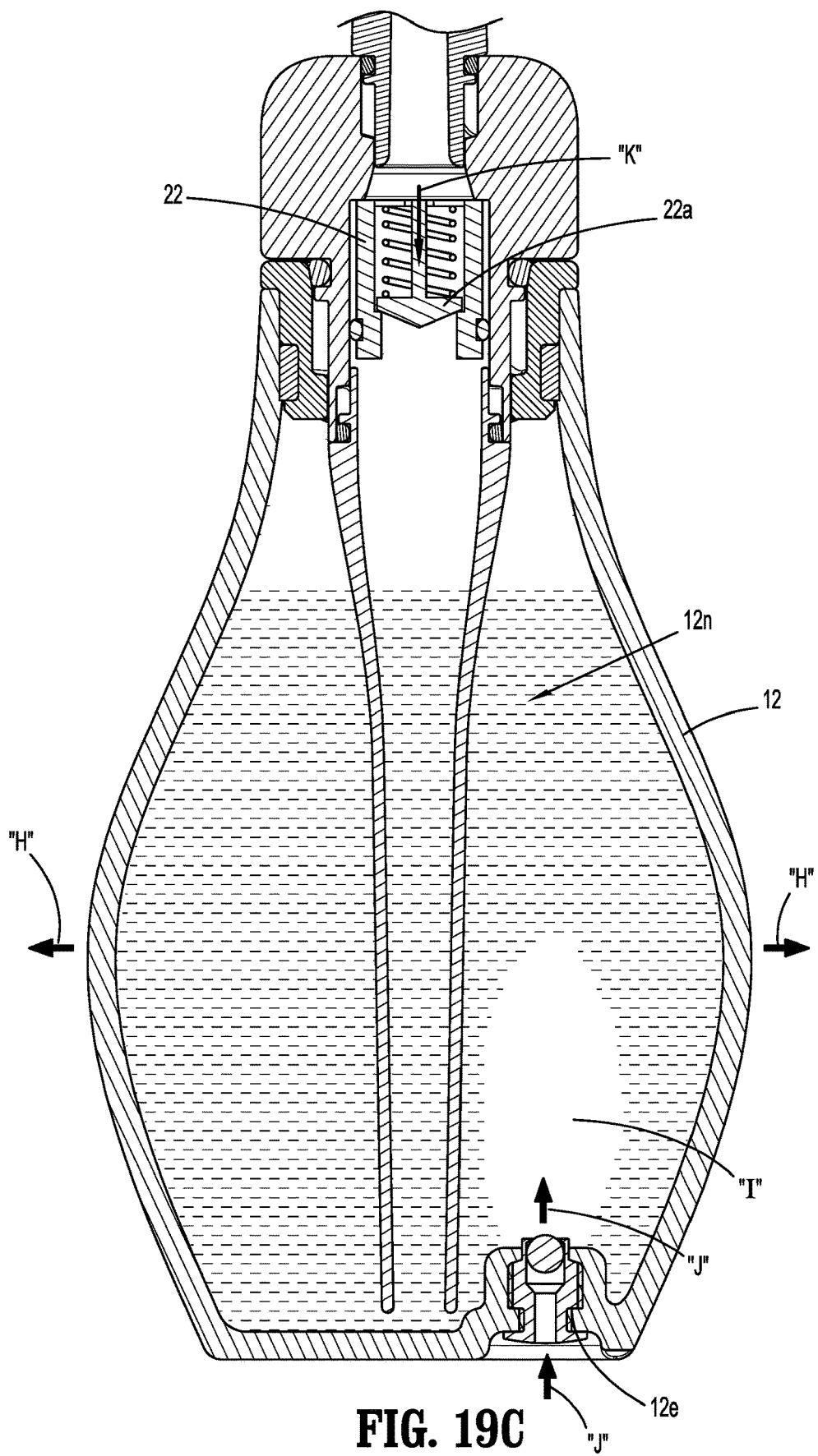

Turning now to FIGS. 5 to 11, the fluid container assembly 12 of the fluid dispensing apparatus 10 includes a fluid container 12*a*, which may be in the form of a flexible bulb, an inlet assembly 12*b* that is secured to a top of the fluid container 12*a*, and an air-inlet valve 12*e* secured to a bottom of the fluid container 12*a*. The inlet assembly 12*b* includes an inlet 12*c* and a gasket 12*d* that is friction-fit around an outer surface of the inlet 12*c*, as indicated by arrows "C" in FIG. 6. The inlet 12*c*, which may be formed of any suitable polymeric material (e.g., plastic) includes a lower lip 12*f* and an upper lip 12*g* that extends radially outward farther than the lower lip 12*f*. Disposed between the lower and upper lips 12*f*, 12*g* of the inlet 12*c* is a plurality of spaced-apart ribs 12*h* that extends around an outer surface of the inlet 12*c*. The inlet 12c defines a central passage 12i therethrough and includes a locking device 12j along an inner surface of the inlet 12c that is substantially similar to the locking device 18q of the cap member 18 for securing the cap member 18 to the inlet 12c via rotation of the cap member 18 relative to the inlet 12c, as illustrated in FIGS. 16-18. In particular, the locking device 12j includes detents 12v that selectively mate with detent recess 18i in the cap member 18. Notably, each of the locking devices and components described herein (e.g., locking devices, locking channels, detents, detent recesses, hands, fingers, etc.) are self-locking quick turn features of all of the respective removable connections that enable the respective components to be quickly secured to another, and to stay locked in place during use, but are configured to be unlocked and/or separated upon relative rotation between the respective components.

The fluid container 12a defines an inlet opening 12k having a plurality of rib channels 12m that is positioned to align with the plurality of spaced-apart ribs 12h of the inlet 12c to facilitate securement of the inlet assembly 12b to the fluid container 12a. The fluid container 12a further defines a fluid cavity 12n configured to support fluid "F" such as water therein.

Figure 10:
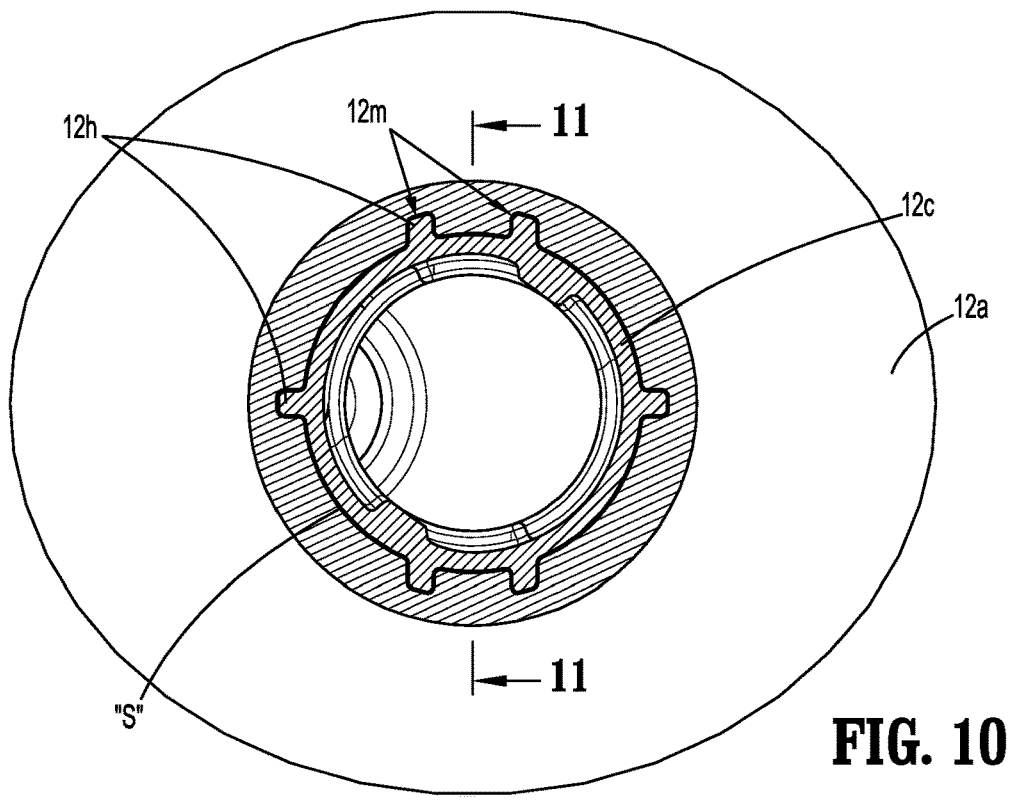
FIG. 10 is an enlarged, cross-sectional view as taken along section line 10-10 shown in FIG. 9.
Figure 11:
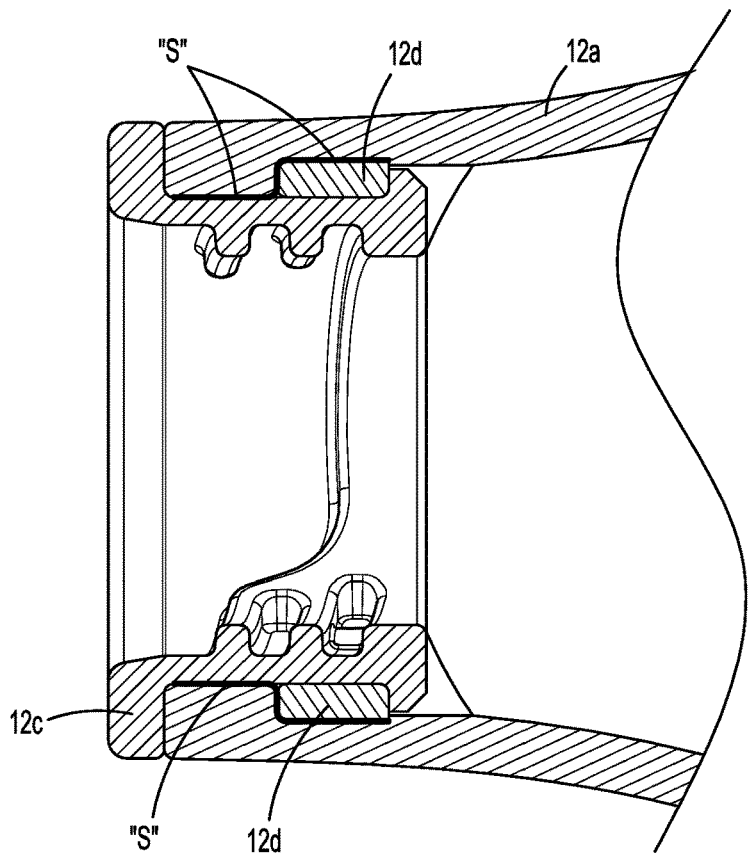
FIG. 11 is an enlarged, cross-sectional view as taken along section line 11-11 shown in FIG. 10.

As shown in FIGS. 7-11, to secure inlet assembly 12b to the fluid container 12a, uncured silicone "S" is applied circumferentially about an inner surface 12x of the fluid container 12a adjacent a bottom end of the plurality of rib channels 12m of the fluid container 12a. With uncured silicone "S" disposed in an uncured bead about the inner surface 12x of the fluid container 12a, the inlet assembly 12b is press-fit into the inlet opening 12k with the plurality of spaced-apart ribs 12h of inlet assembly 12b aligned with, and received by, the plurality of rib channels 12m of the fluid container 12a, as indicated by arrows "D" and "E." In this regard, the upper lip 12g of the inlet assembly 12b seats on top of, and in contact with, an end face 12p of the fluid container 12a. Uncured silicone "S" is then left to cure so that the inlet assembly 12b is secured to the fluid container 12a in sealed engagement therewith to form the fluid container assembly 12 as shown in FIGS. 10 and 11.

As seen in FIGS. 19 and 19A to 19C, in use, with the fluid dispensing apparatus 10 filled with a fluid "F" (e.g., water), the tip member 20 of the fluid dispensing apparatus 10 is inserted into a body cavity such as the rectum or vagina for irrigating the body cavity. The fluid container 12a can then be depressed inwardly, as indicated by arrows "X", to urge the fluid "F" up through the straw member 16 such that the force of the urged fluid "F" pushes the movable disc 22a of the valve assembly 22 distally, as indicated by arrows "G", which compresses the spring 22g of the valve assembly 22 and enables the fluid "F" to pass through the tip member 20 for dispensing the fluid "F" into the body cavity for irrigating, flushing, hydrating and/or otherwise cleaning the body cavity. When the inward depression forces acting on the fluid container 12a are removed, the sidewalls of the fluid container 12a flex back to their original, undepressed position, as indicated by arrows "H", and the valve assembly 22 returns to its original position, as indicated by arrow "K", to reseal the remaining fluid "F" within the fluid cavity 12n. As the fluid container 12a returns to the original position thereof, the air valve 12e of the fluid container assembly 12 opens up to enable air "I" to flow into the fluid cavity 12n to replace the space previously occupied by the fluid "F" that was dispensed from the fluid container 12a, as indicated by arrows "J." Alternatively, as described above, the straw member 16 can be removed so that the fluid dispensing apparatus 10 can open the valve assembly 22 (e.g., a gravity feed) for dispensing fluid "F" by inverting the fluid dispensing apparatus 10. When the straw member 16 is present, the valve assembly 22, namely the spring 22b thereof, has a spring rate sufficiently high to prevent the valve assembly 22 from opening when the fluid dispensing apparatus 10 is inverted.

As seen in FIG. 20, in a fluid dispensing system, multiple tip members 20 and 20' can be provided so that each tip member 20 can be removed and replaced and/or interchanged as desired, for instance, after use for hygienic purposes. The tip members 20 and 20' may be disposable.

Figure 22:
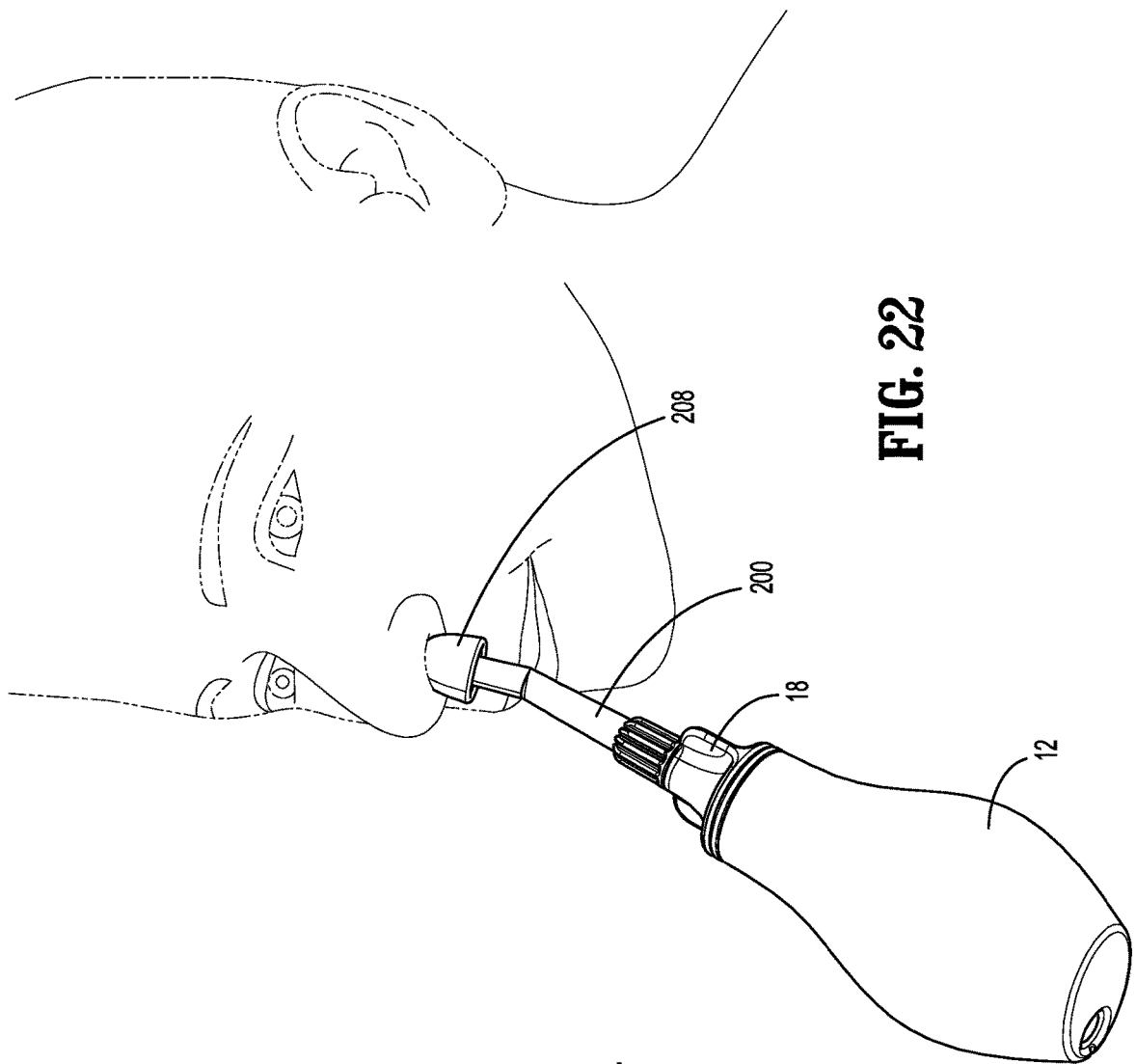
FIG. 22 is a perspective view illustrating the fluid dispensing apparatus of FIG. 21 being utilized for irrigating a user's nasal cavity.
Figure 21:
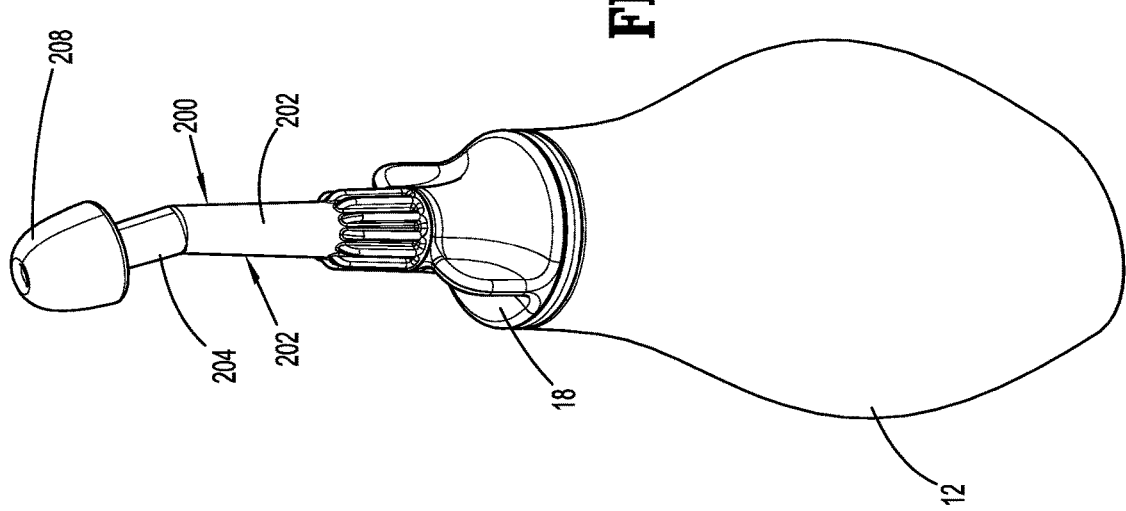
FIG. 21 is a perspective view of another fluid dispensing apparatus including an angled tip assembly in accordance with the principles of this disclosure.

With reference to FIGS. 21 and 22, in aspects, a tip member can be provided in the form of an angled tip member 200 having an angled shaft 202 with a straight segment 204 and an angled segment 206. Angled segment 206 may support a bulbous head 208 to facilitate insertion into and irrigation of, for example, a nasal cavity. The angled tip member 200 can be provided in conjunction with one or more of tip members 20, 20' in a fluid dispensing system, as alternatives to one another.

Figure 23:
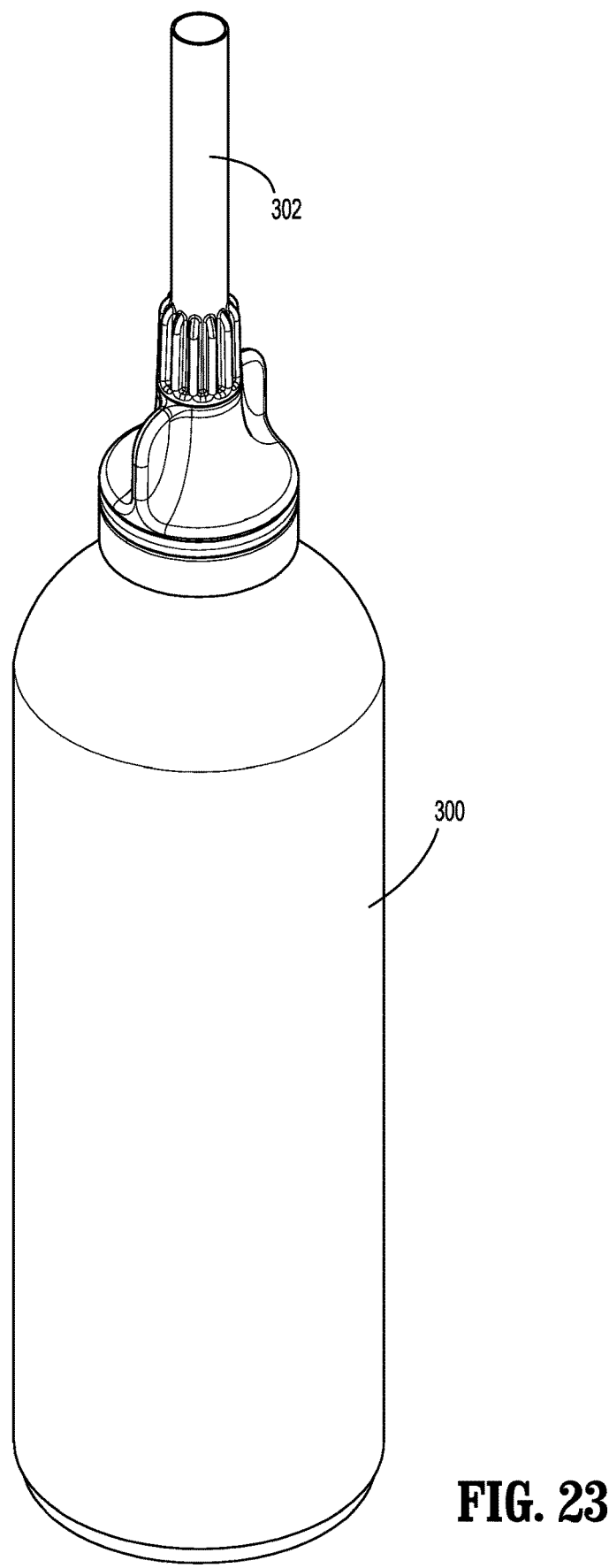
FIG. 23 is a perspective view of still another fluid dispensing apparatus in accordance with the principles of this disclosure.

As seen in FIG. 23, in some aspects, the fluid container 12a may be provided in the form of a water bottle 300 or any other suitable fluid container, which may have a tip member in the form of drinking straw 302.

As can be appreciated, one or more of the components of this disclosure may be disposable and/or reusable and may be formed of any suitable rigid and/or flexible material such as any suitable polymeric material.

The phrases "in an aspect," "in aspects," "in various aspects," "in some aspects," "in other aspects" or the like may each refer to one or more of the same or different aspects in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

Certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The aspects disclosed herein are examples of the disclosure and may be embodied in various forms. For instance, although certain aspects herein are described as separate, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Securement of any of the components of the disclosed devices may be effectuated using known securement techniques such welding, crimping, gluing, fastening, etc.

Persons skilled in the art will understand that the structures and methods specifically described herein and shown in the accompanying figures are non-limiting exemplary aspects, and that the description, disclosure, and figures should be construed merely as exemplary of aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. A fluid dispensing apparatus for irrigating a body cavity, the fluid dispensing apparatus comprising:
   a fluid container assembly defining a longitudinal axis and including a fluid container and an inlet assembly fixedly secured to the fluid container, the inlet assembly and the fluid container having different materials than one another;
   a cap member selectively rotatably attached to the inlet assembly; and
   a tip member selectively attachable to the cap member in response to rotation of the tip member about the longitudinal axis of the fluid container assembly.

2. The fluid dispensing apparatus of claim 1, further comprising a straw member selectively rotatably attached the cap member.

3. The fluid dispensing apparatus of claim 2, wherein the cap member defines a central passage that supports a one-way valve assembly that is disposed in fluid communication with the tip member and a fluid cavity of the fluid container.

4. The fluid dispensing apparatus of claim 3, wherein the cap member includes an actuator portion having a pair of opposed wings that extends from an external surface of the cap member for facilitating rotatable movement of the cap member relative to the fluid container.

5. The fluid dispensing apparatus of claim 4, wherein the actuator portion includes a locking device that extends radially inward from an inner surface of the cap member that defines the central passage, the locking device configured to secure a proximal end portion of the tip member within the cap member.

6. The fluid dispensing apparatus of claim 5, wherein the proximal end portion of the tip member includes a coupling portion, the coupling portion of the tip member includes elongated tabs that project radially outward from an outer side surface of the coupling portion, the elongated tabs configured to cooperate with the locking device within the actuator portion of the cap member to facilitate the selective securement of the coupling portion of the tip member within the cap member.

7. The fluid dispensing apparatus of claim 6, wherein the cap member includes a coupling portion that extends proximally from the actuator portion of the cap member, the coupling portion of the cap member includes elongated tabs that project radially outward from an outer side surface of the coupling portion of the cap member, the elongated tabs of the cap member configured to cooperate with a locking device of the inlet assembly to selectively secure the cap member to the fluid container assembly.

8. The fluid dispensing apparatus of claim 7, wherein the locking device of the inlet assembly includes detents that cooperate with detent recesses defined in the elongated tabs of the cap member to facilitate the selective securement of the coupling portion of the cap member within the inlet assembly.

9. The fluid dispensing apparatus of claim 8, further comprising at least one O-ring that fluidly seals a connection between the cap member and the fluid container, the cap member and the tip member, and/or the cap member and the straw member.

10. The fluid dispensing apparatus of claim 9, further comprising a silicone seal disposed on an inner surface of the fluid container between the inlet assembly and the fluid container to facilitate securement of the inlet assembly to the fluid container.

11. The fluid dispensing apparatus of claim 10, wherein the inlet assembly includes a plurality of spaced-apart ribs and the fluid container defines a plurality of rib channels that receive the plurality of spaced-apart ribs of the inlet assembly to facilitate the securement of the inlet assembly to the fluid container.

12. The fluid dispensing apparatus of claim 11, wherein the inlet assembly includes an upper lip and a lower lip, the upper lip positioned to seat on an end face of the fluid container, the lower lip positioned to support a gasket on an outer surface of the inlet assembly.

13. The fluid dispensing apparatus of claim 12, wherein the fluid container includes an air valve in a bottom surface of the fluid container.

14. The fluid dispensing apparatus of claim 13, wherein the fluid container includes a flexible material that is actuatable upon a squeezing thereof, wherein actuation of the fluid container actuates the one-way valve assembly to enable fluid to pass from the fluid container through the tip member for dispensing the fluid from the tip member.

15. The fluid dispensing apparatus of claim 14, wherein the air valve enables air to enter into the fluid cavity when the fluid container moves from a squeezed position to an unsqueezed position.

16. A fluid dispensing system, comprising:
   a fluid container assembly including a fluid container and an inlet assembly secured to the fluid container by a plurality of rib members extending into the fluid container; and
   a cap assembly selectively attached to the inlet assembly, the cap assembly including at least one tip member and a straw member that are selectively rotatably attachable to the cap assembly, the straw member extending into the fluid container when secured to the cap assembly.

17. The fluid dispensing system of claim 16, wherein the at least one tip member includes a first tip member and a second tip member.

18. The fluid dispensing system of claim 17, wherein at least one of the first or second tip members are disposable.

19. The fluid dispensing system of claim 16, wherein the at least one tip member includes an angled tip member.

20. A fluid dispensing system, comprising:
   a fluid container assembly including a fluid container and an inlet assembly fixedly secured to the fluid container by a silicone seal; and
   a cap assembly selectively attached to the inlet assembly, the cap assembly including at least one tip member having pairs of elongated tab members extending radially outward from an annular sidewall of the at least tip member, the pairs of elongated tabs members being selectively attachable to the cap assembly by a locking device within the cap assembly that interlocks with the pairs of elongated tab members of the at least one tip member.

* * * * *